(12) United States Patent
Lambrecht et al.

(10) Patent No.: US 6,936,072 B2
(45) Date of Patent: Aug. 30, 2005

(54) ENCAPSULATED INTERVERTEBRAL DISC PROSTHESIS AND METHODS OF MANUFACTURE

(75) Inventors: Gregory Lambrecht, Natick, MA (US); Sean Kavanaugh, Eastham, MA (US); Scott Stonebrook, Phoenix, AZ (US)

(73) Assignee: Intrinsic Therapeutics, Inc., Woburn, MA (US)

( * ) Notice: Subject to any disclaimer, the term of this patent is extended or adjusted under 35 U.S.C. 154(b) by 84 days.

(21) Appl. No.: 10/194,428

(22) Filed: Jul. 10, 2002

(65) Prior Publication Data

US 2003/0125807 A1 Jul. 3, 2003

Related U.S. Application Data

(63) Continuation-in-part of application No. 09/696,636, filed on Oct. 25, 2000, now Pat. No. 6,508,839, which is a continuation-in-part of application No. 09/642,450, filed on Aug. 18, 2000, now Pat. No. 6,482,235, which is a continuation-in-part of application No. 09/608,797, filed on Jun. 30, 2000, now Pat. No. 6,425,919.

(60) Provisional application No. 60/311,559, filed on Aug. 10, 2001, provisional application No. 60/304,545, filed on Jul. 10, 2001, provisional application No. 60/149,490, filed on Aug. 18, 1999, provisional application No. 60/161,085, filed on Oct. 25, 1999, and provisional application No. 60/172,996, filed on Dec. 21, 1999.

(51) Int. Cl.[7] ............................................... A61F 2/44
(52) U.S. Cl. ................................. 623/17.16; 623/17.11
(58) Field of Search ....................... 428/138; 156/84–85

(56) References Cited

U.S. PATENT DOCUMENTS

| | | | |
|---|---|---|---|
| 3,526,567 A | * | 9/1970 | Macone ........................ 428/81 |
| 5,100,422 A | | 3/1992 | Berguer et al. |
| 5,171,280 A | | 12/1992 | Baumgartner |
| 5,192,326 A | | 3/1993 | Bao et al. |
| 5,201,729 A | | 4/1993 | Hertzmann et al. |
| 5,239,982 A | | 8/1993 | Trauthen |
| 5,320,644 A | | 6/1994 | Baumgartner |
| 5,370,697 A | | 12/1994 | Baumgartner |
| 5,549,679 A | | 8/1996 | Kuslich |
| 5,552,100 A | | 9/1996 | Shannon et al. |
| 5,571,189 A | | 11/1996 | Kuslich |
| 5,641,373 A | | 6/1997 | Shannon et al. |
| 5,645,597 A | | 7/1997 | Karpiva |
| 5,702,454 A | | 12/1997 | Baumgartner |
| 5,743,917 A | | 4/1998 | Saxon |
| 5,755,797 A | | 5/1998 | Baumgartner |
| 5,785,705 A | | 7/1998 | Baker |

(Continued)

FOREIGN PATENT DOCUMENTS

| | | | |
|---|---|---|---|
| EP | 0 700 671 A1 | 3/1996 | |
| WO | 00/18328 | 4/2000 | |
| WO | WO 00-044288 | 8/2000 | |
| WO | 00/45741 | 8/2000 | |
| WO | WO 0045741 | * 8/2000 | ............. A61F/2/06 |
| WO | WO0128468 A1 | 4/2001 | |
| WO | 01/39696 | 6/2001 | |
| WO | 01/045577 | 6/2001 | |
| WO | 01/52914 | 7/2001 | |
| WO | 02/051622 | 7/2002 | |
| WO | WO 02-058599 | 8/2002 | |
| WO | WO 02-067824 | 9/2002 | |

Primary Examiner—Corrine McDermott
Assistant Examiner—Thomas Barrett
(74) Attorney, Agent, or Firm—Knobbe, Martens, Olson & Bear, LLP; Sean Kavanaugh, Esq.

(57) ABSTRACT

The present invention relates generally to intervertebral disc repair devices and methods of manufacture. A method of manufacturing a dynamically responsive encapsulated intervertebral disc repair device that prevents the flow of disc material out of the disc, provides support to the anulus fibrosus, and shields the nerves of the anulus and spinal cord, is provided.

9 Claims, 10 Drawing Sheets

U.S. PATENT DOCUMENTS

| | | |
|---|---|---|
| 5,800,549 A | 9/1998 | Bao et al. |
| 5,823,994 A | 10/1998 | Sharkey et al. |
| 5,843,173 A | 12/1998 | Shannon et al. |
| 5,888,220 A | 3/1999 | Felt et al. |
| 5,919,235 A | 7/1999 | Husson et al. |
| 5,928,279 A | 7/1999 | Shannon et al. |
| 5,954,716 A | 9/1999 | Sharkey et al. |
| 5,961,545 A | 10/1999 | Lentz et al. |
| 5,976,192 A | 11/1999 | McIntyre et al. |
| 6,001,056 A | 12/1999 | Jassawalla et al. |
| 6,007,570 A | 12/1999 | Sharkey et al. |
| 6,019,793 A | 2/2000 | Perren et al. |
| 6,073,051 A | 6/2000 | Sharkey et al. |
| 6,099,791 A | 8/2000 | Shannon et al. |
| 6,102,930 A | 8/2000 | Simmons, Jr. |
| 6,120,539 A | 9/2000 | Eldridge et al. |
| 6,124,523 A | 9/2000 | Banas et al. |
| 6,126,682 A | 10/2000 | Sharkey et al. |
| 6,132,465 A | 10/2000 | Ray et al. |
| 6,140,452 A | 10/2000 | Felt et al. |
| 6,146,380 A | 11/2000 | Racz et al. |
| 6,203,735 B1 | 3/2001 | Edwin et al. |
| 6,214,039 B1 | 4/2001 | Banas et al. |
| 6,224,630 B1 | 5/2001 | Bao et al. |
| 6,245,099 B1 | 6/2001 | Edwin et al. |
| 6,245,107 B1 | 6/2001 | Ferree |
| 6,264,695 B1 | 7/2001 | Stoy |
| 6,267,834 B1 | 7/2001 | Shannon et al. |
| 6,273,912 B1 | 8/2001 | Scholz et al. |
| 6,280,475 B1 | 8/2001 | Bao et al. |
| 6,312,462 B1 | 11/2001 | McDermott et al. |
| 6,355,063 B1 | 3/2002 | Calcote |
| 6,371,990 B1 | 4/2002 | Ferree |
| 6,383,214 B1 | 5/2002 | Banas et al. |
| 6,398,803 B1 | 6/2002 | Layne et al. |
| 6,416,537 B1 | 7/2002 | Martakos et al. |
| 6,419,704 B1 | 7/2002 | Ferree |
| 6,428,576 B1 | 8/2002 | Haldimann |
| 6,520,967 B1 | 2/2003 | Cauthen |
| 6,579,291 B1 | 6/2003 | Keith et al. |
| 6,726,696 B1 * | 4/2004 | Houser et al. ............... 606/151 |
| 2002/0007218 A1 | 1/2002 | Cauthen |
| 2002/0077701 A1 | 6/2002 | Kuslich |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147496 A1 | 10/2002 | Belef et al. |
| 2002/0151980 A1 | 10/2002 | Cauthen |
| 2002/0165542 A1 | 11/2002 | Ferree |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0040796 A1 | 2/2003 | Ferree |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2004/0002764 A1 | 1/2004 | Gainor et al. |

\* cited by examiner

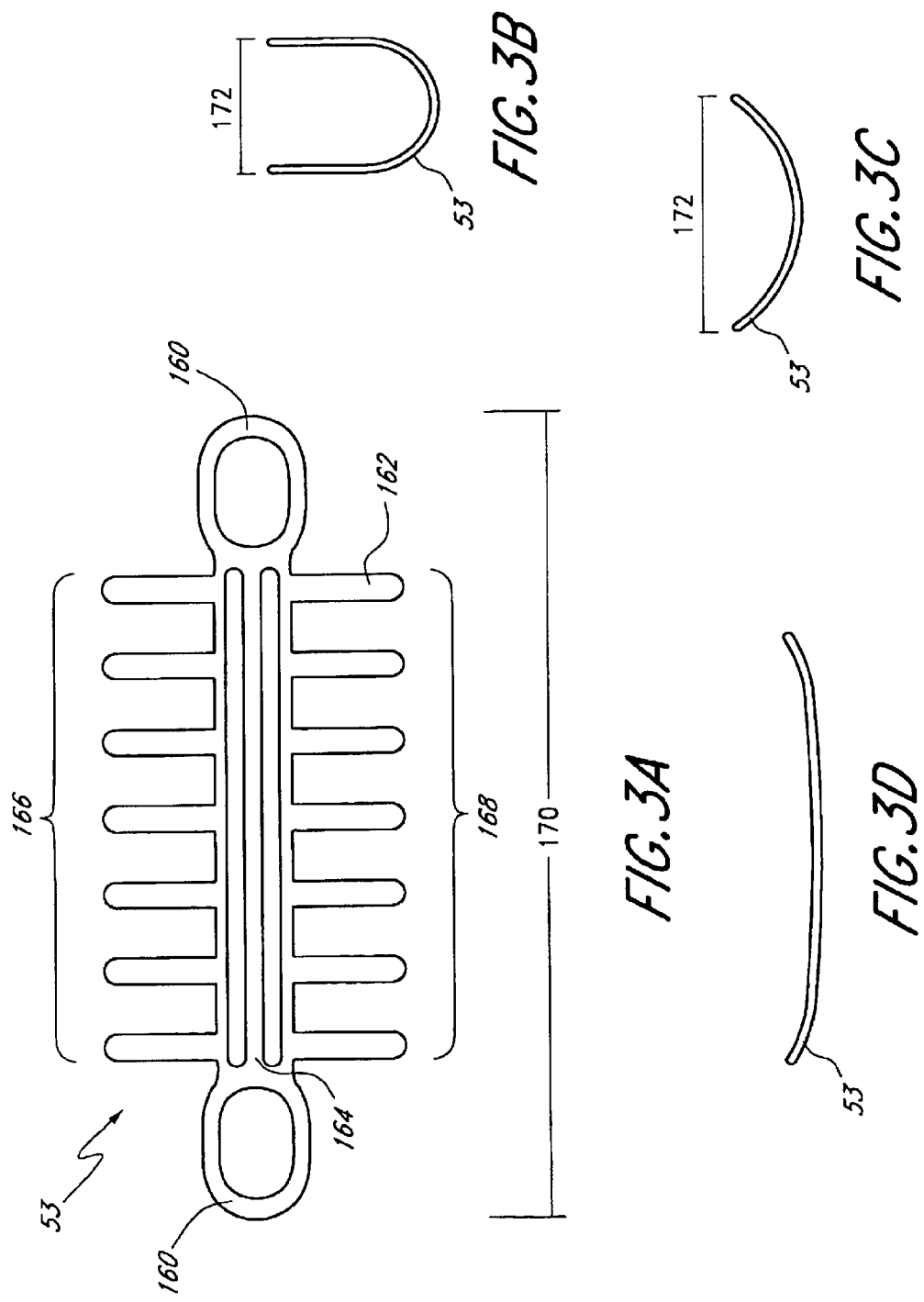

ENCAPSULATED INTERVERTEBRAL DISC PROSTHESIS AND METHODS OF MANUFACTURE

RELATED APPLICATIONS

This application is a continuation-in-part of U.S. application Ser. No. 09/696,636 filed on Oct. 25, 2000 now U.S. Pat. No. 6,508,839 which is a continuation-in-part of U.S. application Ser. No. 09/642,450 filed on Aug. 18, 2000, now U.S. Pat. No. 6,482,235 which is a continuation-in-part of U.S. application Ser. No. 09/608,797 filed on Jun. 30, 2000, now U.S. Pat. No. 6,425,919 and claims benefit to U.S. Provisional Application No. 60/311,559 filed Aug. 10, 2001, U.S. Provisional Application No. 60/304,545 filed Jul. 10, 2001, U.S. Provisional Application No. 60/149,490 filed Aug. 18, 1999, U.S. Provisional Application No. 60/161,085 filed Oct. 25, 1999 and U.S. Provisional Application No. 60/172,996 filed Dec. 21, 1999, the entire teachings of these applications being incorporated herein by reference.

BACKGROUND OF THE INVENTION

1. Field of the Invention

The present invention relates generally to intervertebral disc devices suitable for delivery into a body to treat injured discs or to improve the function of non-injured discs.

2. Background

Methods of encapsulating a new intervertebral prosthesis are not known in the art. The most relevant prior art can be found in references concerning the encapsulation of stents and grafts in flexible biocompatible materials. However, these references are limited to teaching the coating of certain cylindrical structures with a single or double-sided coating of expanded polytetrafluoroethylene. These teachings do not address some or all of the requirements of a new intervertebral disc device which may be semicircular in cross-section, collapsible, fatigue resistant, biocompatible, and suitable for the dynamic disc environment.

Fluoropolymer tubings and other extruded or expanded polymer products are well known in the art and can provide an excellent material for encapsulation. Expanded polytetrafluoroethylene (ePTFE) is made by expanding polytetrafluoroethylene (PTFE) tubing or sheet material under controlled conditions during the manufacturing process. This process alters the physical properties of the material by creating microscopic pores in the structure of the material. The resulting material is imparted with unique physical properties that make it ideal for use in medical devices, electronic insulators, high performance filters, and a host of other applications. Material made from ePTFE differs from regular PTFE in that the material is microporous, soft, very flexible, has a lower dielectric constant, increased linear strength, and improved biocompatibility.

The structure of ePTFE is unique in that the material is made up of a number of solid nodes inter-connected by a matrix of thin fibrils. The gaps, or pores, between the fibrils are what allows the material to excel in applications requiring cellular ingrowth. ePTFE is also utilized for its endothelization and thrombogenic properties. Both ePTFE and PTFE resin have long been utilized for implantable medical devices due to their inertness and biocompatibility. The amount of expansion in ePTFE is usually referred to as internodal distance (IND). IND is a measure of the average distance between the material's nodes. ePTFE is commonly available from manufacturers in IND sizes ranging from $5\mu$ to over $200\mu$. IND plays a role in the softness, flexibility, and degree of potential ingrowth that the material exhibits. Some commercial suppliers of ePTFE sinter the outside of the material after the expansion process in order to make it more durable and smooth.

Other useful PTFE based materials known in the art are PTFE resin aqueous dispersions or "aqueous PTFE" and heat shrinkable PTFE. Aqueous PTFE is commonly comprised of milky white dispersions of PTFE particles in water stabilized by wetting agents. Its composition is usually 30 to 60 percent PTFE particles and the remainder is comprised of water and a nonionic surfactant. Objects can be dip-coated with repeated passes into aqueous PTFE until the final desired thickness is obtained. The water can then be removed and the other ingredients deactivated. The melting temperature of these resins are around 325° Celsius. The dried resin particles can be coalesced by heat into a continuous coating or the substrate can remain coated, or impregnated, with unmelted particles. Both glass fabric and synthetic substrates can be processed.

Heat shrinkable PTFE tubing is well known in the art and provides a method for application of a tight, protective covering to items that will be subjected to the extremes of heat, corrosion, shock, moisture, and other critical environmental conditions. Shrinkable PTFE tubing requires around 340° Celsius to recover. Upon reaching approximately 330° the PTFE goes into the "gel" state (amorphous from crystalline). PTFE begins to shrink at 340° and completes its recovery during the cooling cycle.

This disclosure utilizes particular orthopedic references, nomenclature, and conventions. Accordingly, several background figures and descriptions are included to aid in the understanding of the environment under which specific embodiments of the invention may be used. FIGS. 1A and 1B show the general anatomy of a functional spine unit 345. In this description and the following claims, the terms 'anterior' and 'posterior', 'superior' and 'inferior' are defined by their standard usage in anatomy, i.e., anterior is a direction toward the front (ventral) side of the body or organ, posterior is a direction toward the back (dorsal) side of the body or organ; superior is upward (toward the head) and inferior is lower (toward the feet).

SUMMARY OF THE INVENTION

The invention relates generally to methods of manufacture of intervertebral disc devices suitable for delivery into a body to treat injured or poorly functioning discs or to reinforce healthily discs.

In one or more of the several embodiments, the present invention provides for an intervertebral disc prosthesis that is biocompatible, collapsible, concave shaped, and sized to fit within the area defined by the superior and inferior end plates and outermost lamella of the anulus fibrosus of a functional spinal unit.

It is further objective of one or more of several embodiments of this invention to provide a device useful in shielding the nerves of the anulus and spinal cord from pressure and or chemicals within the disc.

It is a further objective of one or more of various embodiments to provide a device that provides support to a weakened or healthy anulus in an intervertebral disc.

It is a further object in one or more of the several embodiments to provide a method for the manufacture of one or more of the several embodiments of the invention.

It is a further object to provide in one or more of the several embodiments an encapsulating covering that is permanently retained on an intervertebral barrier device and substantially isolates it from bodily tissue.

It is a further objective of one or more of various embodiments to provide a method of encapsulating an intervertebral prosthesis in a biocompatible material that does not interfere with the deformation and flexibility of the barrier frame.

It is another object of several embodiments of the invention to provide a method of making an intervertebral disc implant by providing a barrier frame having first and second sides, positioning a first membrane adjacent the first side and a second membrane adjacent the second side, applying force so that the first membrane contacts the second membrane at one or more points and heating the first and second membrane to form bonds at one or more of those points. The first membrane may be attached to the second membrane. In one embodiment, the first membrane and second membrane may be opposing sides of an envelope. In a preferred embodiment, the first and/or second membrane is an ePTFE membrane. In another embodiment, a portion of the membrane is positioned beyond the frame or its periphery.

It is yet another object of the current invention to provide a method for making an intervertebral prosthesis by placing a first encapsulating material over a mandrel, placing a device frame on the first encapsulating material, placing a second encapsulating material on top of the device frame, placing a mandrel cover on top of the second encapsulating material and applying force so that the edges of the first and second encapsulating material form contact points with each other around the device frame and heating the mandrel and/or cover until the first and second encapsulating material bond to each other at the contact points, thereby encapsulating the frame.

It is yet another object of the current invention to provide a method for making an intervertebral prosthesis by placing a first biocompatible encapsulating material over a heatable mold with a curved face, the material being sized to extend from about 0.1 mm to about 0.5 mm beyond the edges of a barrier frame. The barrier frame, which is dimensioned to span beyond the distance defined by the maximum distance between an inferior and superior endplate of a normal intervertebral disc and to extend circumferentially along the lateral and posterior surfaces of an anulus, the barrier having a semi-circular cross-section and comprised of nickel titanium alloy, is placed on the first encapsulating material. A second encapsulating material, designed to extend from about 0.1 mm to about 5 mm beyond the edges of the barrier frame, is placed on top of the device frame. A mold cover with a concave interior corresponding to face of the mold on top of the second encapsulating material is placed on top of the device frame. Force is then applied such that the edges of the first and second encapsulating material form one or more contact points with each other around the barrier frame. The base and/or the cover and/or the frame sandwiched between the first and the second encapsulating material is heated until the first and second encapsulating material bond to each other at said one or more contact points.

It is a further object of various embodiments of the present invention to provide a method for making an intervertebral prosthesis by placing a first biocompatible encapsulating material over a heatable mold with a curved face, where the curved face has a first axis and a second axis which are perpendicular to one another. The first axis is a longitudinal axis which has a first radius of curvature and the second axis is a transverse axis which has a second radius of curvature. The first radius of curvature has a range of about 0.1 cm to about 4 cm and the second radius of curvature has a range of about 2.0 cm to about 7.0 cm. Alternatively, the device can be 'U' shaped in the transverse orientation and preferably has lateral legs in the range of about 0.1 cm to about 2.0 cm that protrude perpendicularly through a gradual curve with an inner diameter in the range of about 0.2 cm to about 1.5 cm.

BRIEF DESCRIPTION OF THE DRAWINGS

The foregoing and other objects, features and advantages of the invention will be apparent from the following more particular description of preferred embodiments of the invention as illustrated in the accompanying drawings in which like reference characters refer to the same parts throughout the different views. The drawings are not necessarily to scale, emphasis instead being placed upon illustrating the principles of the invention.

FIG. 1A is a view of a transverse section, and FIG. 1B is a view of a sagittal section. FIG. 1C is a view of a transverse section of the functional spine unit and shows a defect in the anulus which could have been created iatrogenically as in the performance of an anulotomy or naturally occurring. FIG. 1D is a view of a transverse section of the spine unit with a defect in the anulus that does not extend completely through the anulus.

FIGS. 3A–3C show the device frame. FIG. 3A shows a front view of the frame.

FIGS. 3B, 3C and 3D show embodiments of the frame with different frame heights and curvatures.

DETAILED DESCRIPTION OF THE PREFERRED EMBODIMENT

Figure 1A:
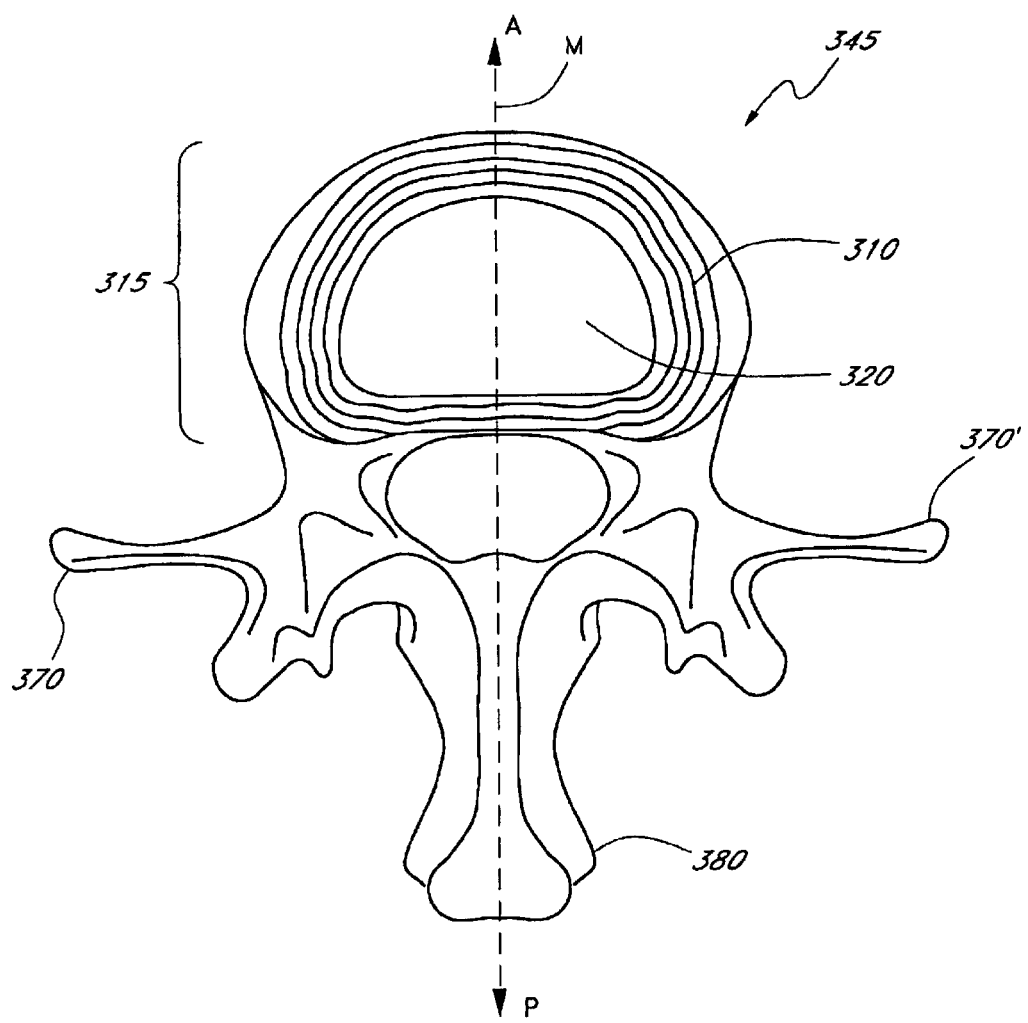
FIGS. 1A and 1B show the general anatomy of a functional spinal unit.

The environment in which various embodiments of the present invention find greatest utility is within a human intervertebral disc that has a weakened or compromised anulus. FIG. 1A is an axial view along the transverse axis M of a vertebral body with the intervertebral disc 315 superior to the vertebral body. Axis M shows the anterior (A) and posterior (P) orientation of the functional spine unit within the anatomy. The intervertebral disc 315 contains the anulus fibrosus 310, which surrounds a central nucleus pulposus 320. Also shown in this figure are the left 370 and right 370' transverse spinous processes and the posterior spinous process 380.

Figure 1B:
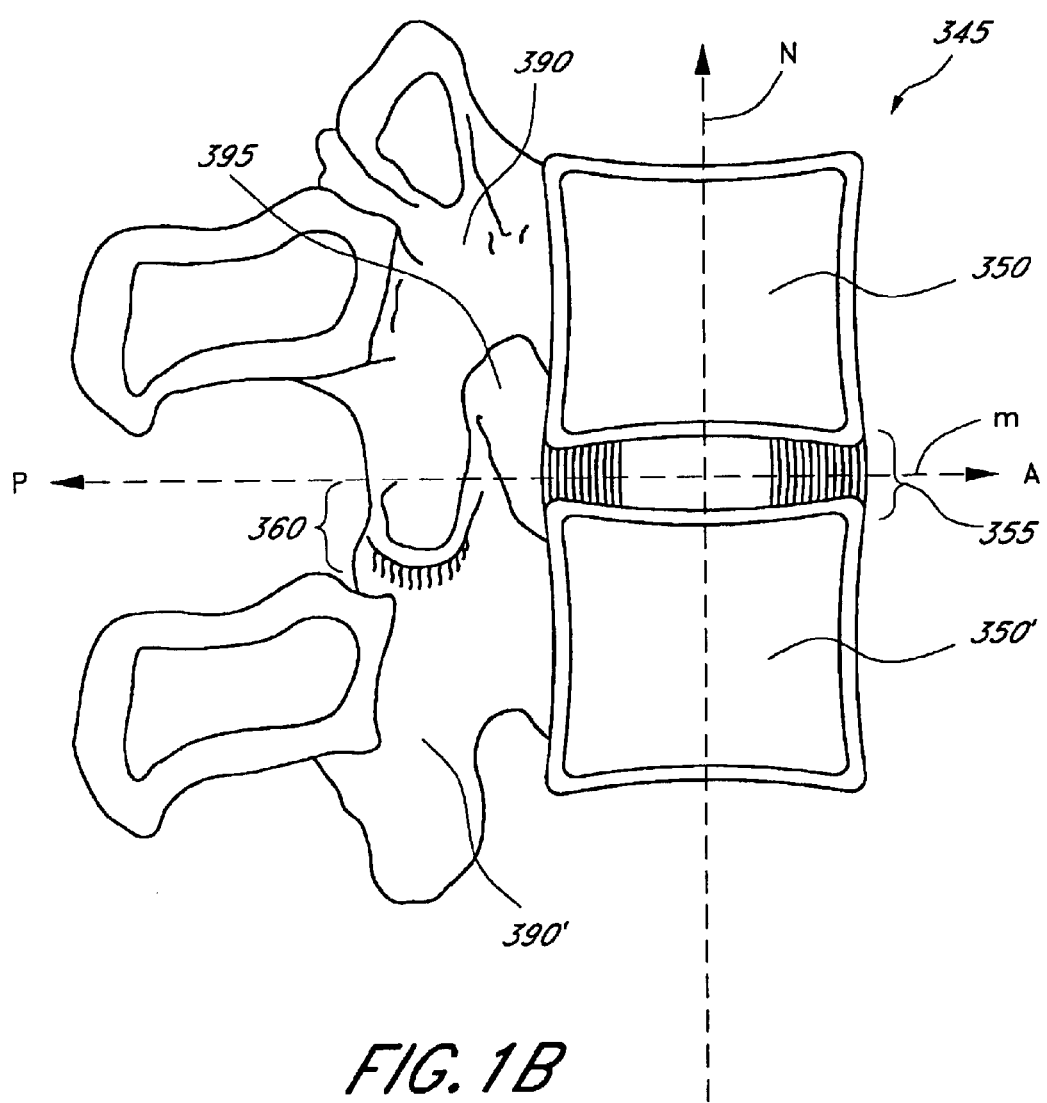

FIG. 1B is a sagittal section along sagittal axis N through the midline of two adjacent vertebral bodies 350 (superior) and 350' (inferior). Intervertebral disc space 355 is formed between the two vertebral bodies and contains intervertebral disc 315, which supports and cushions the vertebral bodies and permits movement of the two vertebral bodies with respect to each other and other adjacent functional spine units.

Intervertebral disc 315 is comprised of the outer anulus 310 which normally surrounds and constrains the nucleus 320 to be wholly within the borders of the intervertebral disc space. Axis M extends between the anterior (A) and posterior (P) of the functional spine unit. The vertebrae also include facet joints 360 and the superior 390 and inferior 390' pedicle that form the neural foramen 395.

Figure 1C:
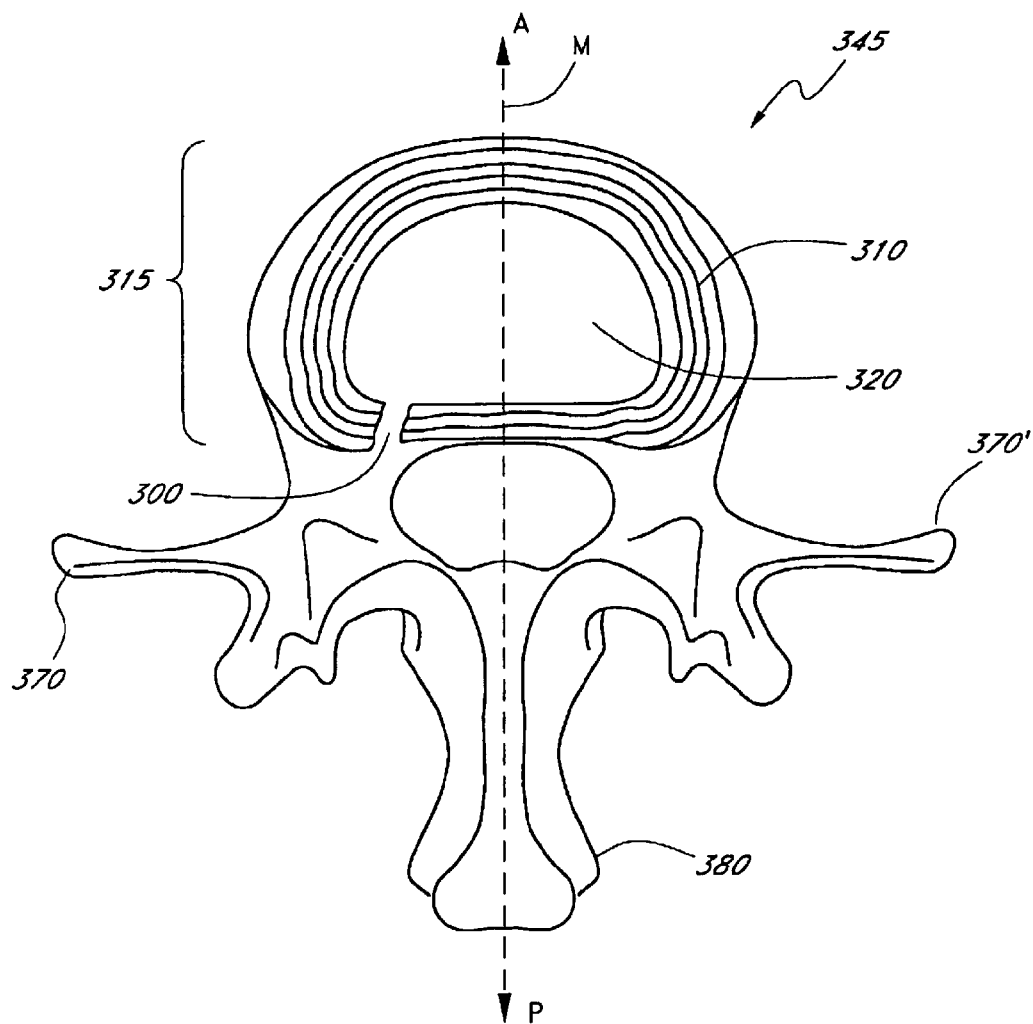
FIGS. 1C and 1D show a functional spine unit with a defect in the anulus.
Figure 1D:
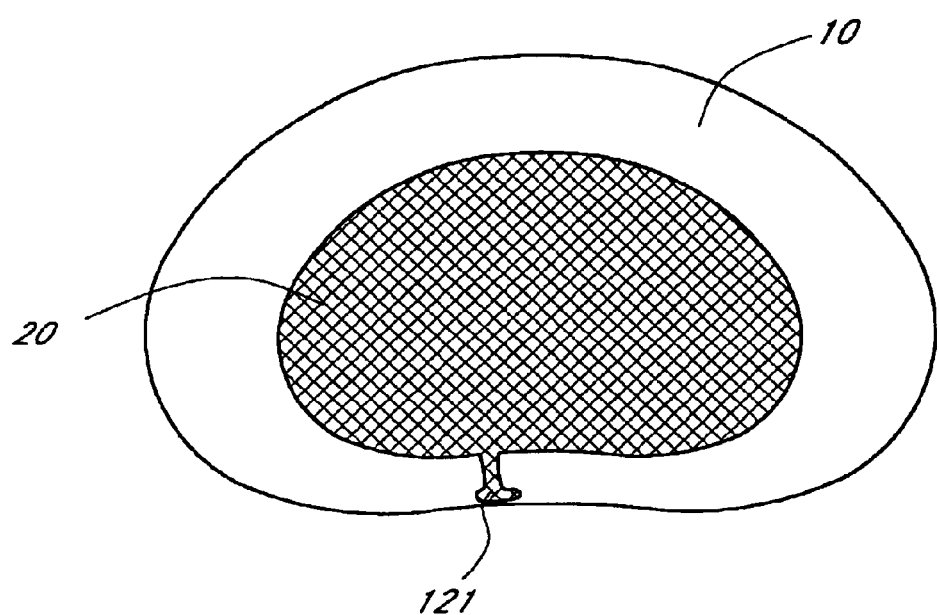

FIG. 1C is an axial view of the anulus 310 and nucleus 320 wherein the anulus has a partial defect that does not completely perforate the anulus 310. FIG. 1C shows a spine unit with a iatrogenic or naturally occurring hole 300 in the anulus 310. This condition can cause pain and diminishes the function of the disc because of a loss of intervertebral pressure and disc height. FIG. 1D shows a cross sectional view of a spine unit with a defect 121 in the posterior anulus 310 in which the perforation of the tissue is partial. In this condition, the anulus 310 is weakened and may protrude when loaded but does not permit the egress of nucleus 320 tissue outside of the disc.

In several of embodiments herein, the present invention provides a device for sealing or reinforcing defects in tissue walls separating two anatomic regions of the body and to methods of making such device. Alternatively, one or more of the several embodiments of the device may be used to provide support to tissue walls that do not exhibit holes but are nonetheless weakened and can benefit from an implanted support structure. Also, prosthetic devices and method of their manufacture are disclosed which provide the closure or support of a defect in the anulus of the human intervertebral disc, preventing the egress of material from within the disc and/or distributing pressure within the disc space across an inner wall surface of the disc.

Closure of the defect and/or support of the weakened sector comprising the defect can be achieved by placing a membrane or barrier device on an interior aspect of the defect. In the case of the intervertebral disc, the device 120 is positioned either on the interior aspect of the anulus proximate to the nucleus or between layers of the AF. The device 120 may be inserted in the desired location after dissecting a space between the anulus and nucleus. Alternatively, a portion of the nucleus and/or anulus may be resected to create adequate space. Ideally, the device 120 is inserted through a defect in the anular surface or through a minimally invasive iatrogenic hole 300. Such a hole is shown in FIG. 1D.

Figure 2A:
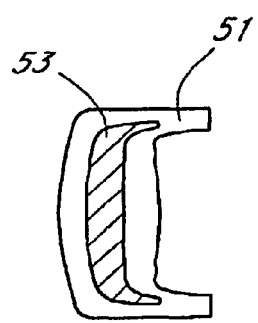
FIGS. 2A and 2B are side and front views of the device of the present invention.
Figure 2B:
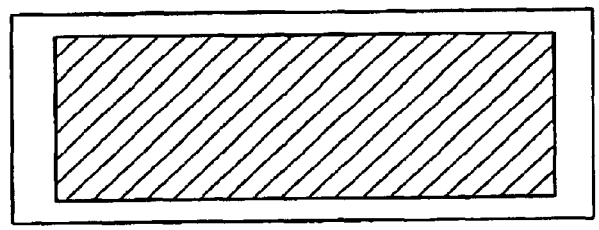

FIGS. 2A and 2B depict an intervertebral disc device 120 comprising an encapsulating or covering membrane or material 51 and a dynamic support frame 53. The concave portion of the device preferably faces the nucleus 20 while the convex surface faces the defect 16 and the inner aspect of the anulus 10. This embodiment exploits pressure within the disc to compress device 120 against neighboring vertebral bodies 50 and 50' to aid in sealing. The 'C' shape cross-section as shown in FIG. 2A is the preferred shape of the device 120 wherein the convex portion of the barrier or patch rests against the interior aspect of the anulus while the concave portion faces the nucleus. To improve the sealing ability of such a device 120, the upper and lower portions of this 'C' shaped device are positioned against the vertebral endplates or overlying cartilage. As the pressure within the nucleus increases, these portions of the patch are pressurized toward the endplates with an equivalent pressure, preventing the passage of materials around the device. Dissecting a matching cavity prior to, or during device placement, can expedite the implantation of such a 'C' shaped patch.

Figure 4:
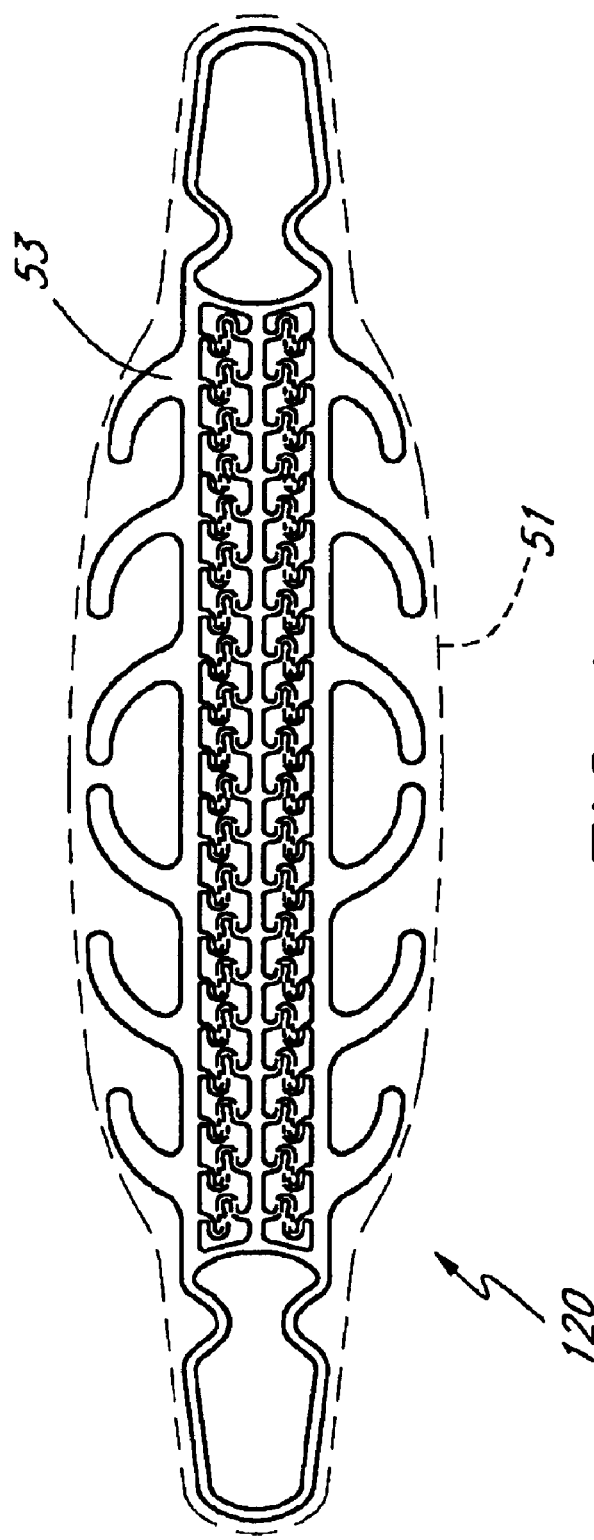
FIG. 4 shows a front view of the device with an encapsulated frame.
Figure 5A:
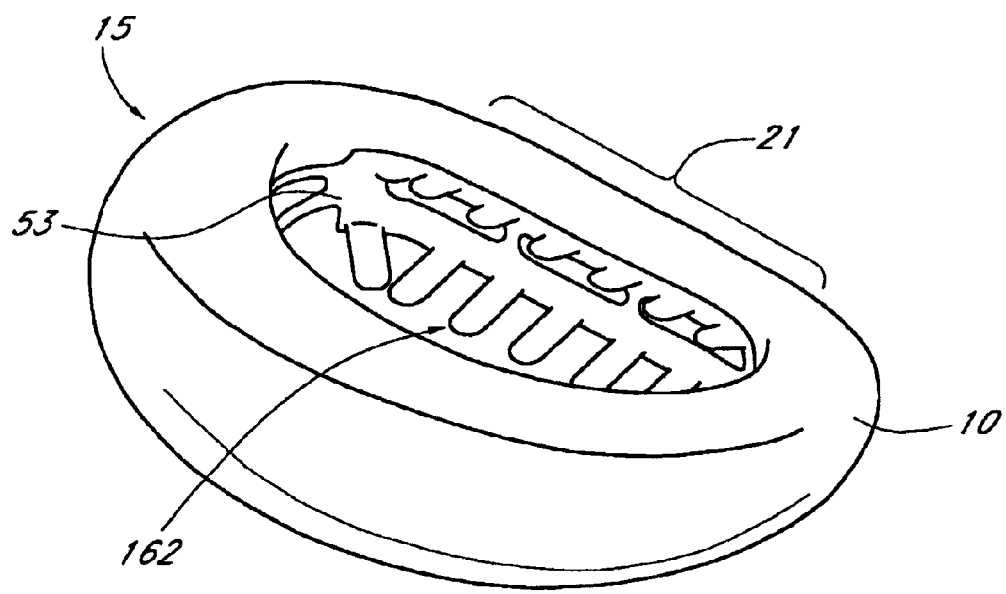
FIGS. 5A and 5B illustrate perspective views of the barrier frame mounted within an intervertebral disc.
Figure 5B:
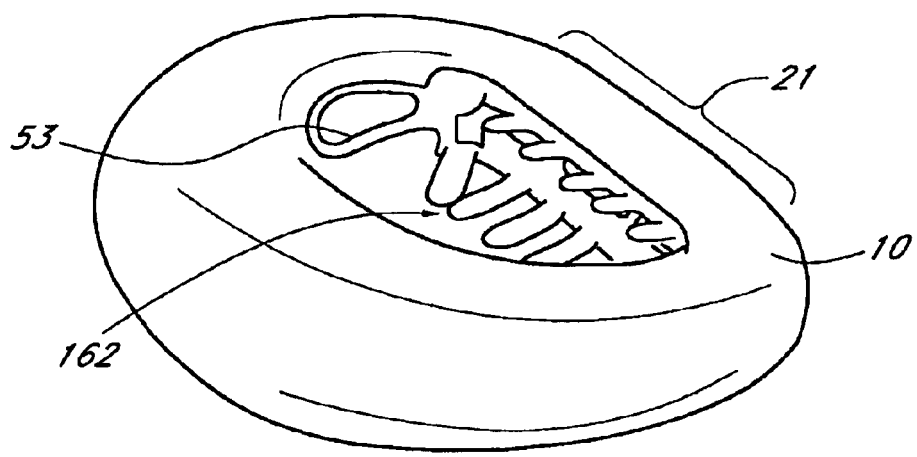

The geometries of the support frame 53 shown in FIGS. 3, 4 and 5 can preferably be formed from a relatively thin sheet of material. The material may be a polymer, metal, or gel, however, the superelastic properties of nickel titanium alloy (NITINOL) makes this metal particularly advantageous in this application. Sheet thickness can generally be in a range of about 0.002 inches to about 0.080 inches and for certain embodiments has been found to be optimal if between about 0.003 inches to about 0.015 inches, for the thickness to provide adequate expansion force to maintain contact between the covering material 51 and surrounding vertebral endplates. The pattern may be Wire Electro-Discharge Machined (EDM), cut by laser, chemically etched, or formed by other suitable means.

FIG. 3A shows an embodiment of a frame 53 having a superior edge 166 and an inferior edge 168. The frame 53 can form a frame of device 120. This embodiment comprises dissecting surfaces or ends 160, radial elements or fingers 162 and a central strut 164. The circular shape of the dissecting ends 160 aids in dissecting through the nucleus pulposus 20 and/or along or between an inner surface of the anulus fibrosus 10. Alternatively, the ends 160 may be blunt and fully encapsulated in the covering material 51. The distance between the left-most and right-most points on the dissecting ends is the frame length 170. This length 170 preferably lies along the inner perimeter of the posterior anulus following implantation. The frame length 170 can be as short as 3 mm and as long as the entire interior perimeter of the anulus fibrosus. The superior-inferior height of these dissecting ends 160 is preferably similar to or larger than the posterior disc height.

This embodiment employs a multitude of fingers 162 to aid in holding the membrane against the superior and inferior vertebral endplates. The distance between the superior-most point of the superior finger and the inferior-most point on the inferior finger is the frame height 172. This height 172 is preferably greater than the disc height at the inner surface of the posterior anulus. The greater height 172 of the frame 53 allows the fingers 162 to deflect along the superior and inferior vertebral endplates, enhancing the seal of the device 120 against egress of material from within the disc 15.

The spacing between the fingers 162 along the frame length 170 can be tailored to provide a desired stiffness of the frame 53. Greater spacing between any two neighboring fingers 162 can further be employed to insure that the fingers 162 do not touch if the frame 53 is required to take a bend along its length. The central strut 164 can connect the fingers and dissecting ends and preferably lies along the inner surface of the anulus 10 when seated within the disc 15. Various embodiments may employ struts 164 of greater or lesser heights and thicknesses to vary the stiffness of the overall frame 53 along its length 170 and height 172.

FIGS. 3B, 3C and 3D show a cross sectional view of the device frame 53 with different frame heights 172 and curvatures to accommodate different anatomical applications. In a preferred embodiment, the curved face has a first axis and a second axis which are perpendicular to one another. The first axis is a longitudinal axis which has a first radius of curvature and the second axis is a transverse axis which has a second radius of curvature. Preferably, the two radii are not equal to one another. The first radius of curvature has a range of about 0.1 cm to about 4 cm, preferably from about 0.2 cm to about 2.5 cm, more preferably about 0.97 cm. The second radius of curvature has a range of about 2.0 cm to about 7.0 cm, preferably from about 3.0 cm to about 5.0 cm.

In an alternative embodiment, the device can be 'U' shaped in the transverse orientation and preferably has lateral legs in the range of about 0.1 cm to about 2.0 cm, preferably in the range of about 0.5 cm to about 1.3 cm, that protrude perpendicularly through a gradual curve with an inner diameter in the range of about 0.2 cm to about 1.5 cm.

FIG. 4 shows another embodiment of the barrier frame 53 encapsulated in the membrane or encapsulating material 51 to form the device 120.

Figure 6A:
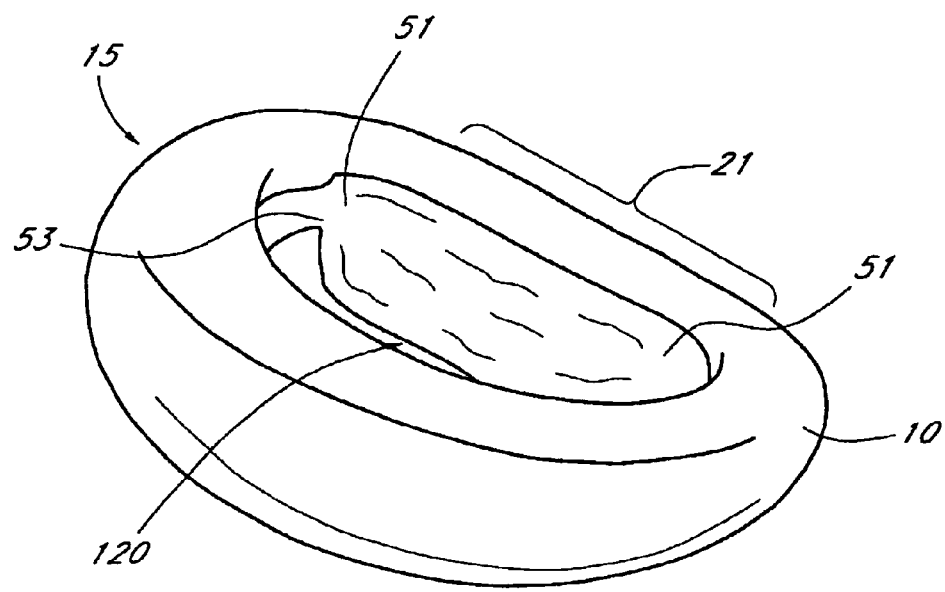
FIGS. 6A and 6B illustrate perspective views of the device mounted within an intervertebral disc.
Figure 6B:
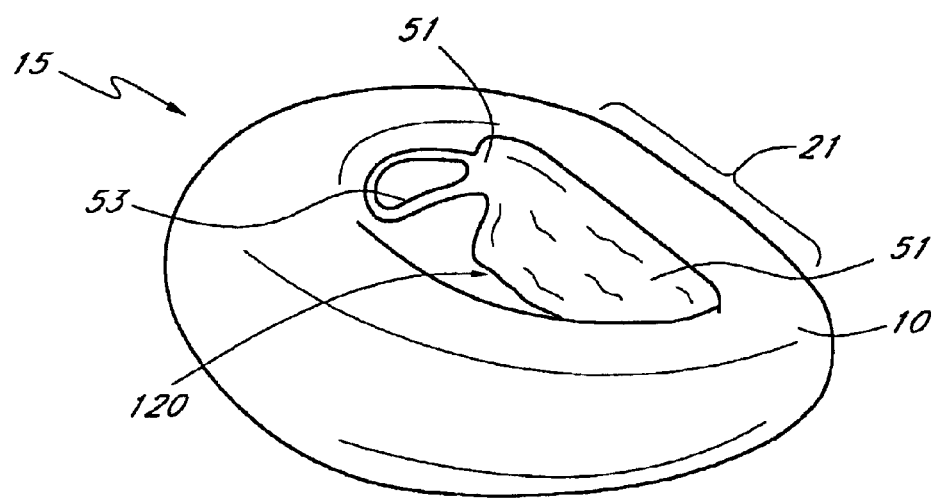

FIGS. 5A and B show the barrier frame 53 within a disc. FIGS. 6A and B show the barrier frame 53 and encapsulating material 51 of the device 120 within a disc situated in front of the posterior anulus.

The encapsulating membrane or material 51 of the device 120 may be a relatively soft, smooth, and flexible biocompatible material so that the device 120 does not injure the intra anular walls or superior and inferior endplates. Biocompatality and inertness are also important so that there is minimal physiological reaction to the device 120. The material(s) comprising the encapsulating material 51 can be impermeable to liquid transfer such that its surface does not permit travel of disc tissue through its surface and outside the disc. Accordingly, the preferred embodiment is made of ePTFE, which exhibits these properties. ePTFE is also strong and resilient enough to withstand the high pressure and dynamic environment found in the intervertebral disc and aids in the devices ability to seal defects and shield nerves in the anulus. Preferably, the internodal distance of the ePTFE, i.e., the average distance between the material's nodes, ranges from $0.\mu$ to over $200\mu$. As will be further discussed, the encapsulating membrane 51 can filly or partially encapsulate the frame 53 or merely form a portion of a single side of the frame 53.

Though the preferred embodiment of the device 120 utilizes ePTFE for the encapsulating material 51 other suitable biocompatible materials may be used. For example, the membrane may alternatively comprise biologic materials such as keratin, collagen, bio-engineered anulus fibrosus, protein polymers or the like. Other suitable synthetic materials include polyamides, polyimides, silicones, polyurethane, natural rubber, latex and other fluoropolymers such as perfluoroalkoxy (PFAs) and fluorinated ethylenepropylene (FEP). These materials can be affixed to the barrier frame through compression molding, solvent bonding, injection molding, or through in situ polymerization.

In one embodiment of the invention, the encapsulating material or membrane 51 can be fixed to the frame 53 by sutures. The frame 53 may simply be encapsulated in ePTFE material by suturing two pieces of material around the periphery of the frame 53. Also, to minimize the amount of stitches, a single folded piece of material or a tube may be used. This method provides a very durable attachment between the two pieces of material and yet permits the device to flex evenly. Suturing the encapsulating material 51 to the frame 53 can also permit the frame 53 to move or flex relatively unimpeded by the encapsulating material 51. Suturing is also advantageous because it is strong, reliable, finely detailed, and will not harm the disc. In addition to suturing along the periphery of the frame 53, the fingers 162 and internal geometry of the frame may be secured to the encapsulating material by suturing.

Ultrasonic welding may also be used as above to bond the edges of the ePTFE to each other around the periphery of the barrier frame 53. Because of the intense heat delivered by this method, the mechanical properties of the ePTFE may be different at the weld. This can be reduced by selectively welding the encapsulating material at measured points spanning the periphery of the barrier frame including between the fingers 162 and between other voids in the geometry.

In a preferred method of manufacturing the device 120, the frame 53 is encapsulated in ePTFE by first making a sandwich-like arrangement 300 of the frame 53 and a first 54 and second encapsulating material 55. Each of the encapsulating material 54 and 55 is comprised of a thin sheet of ePTFE that is patterned to extend around from about 0.004 inches to about 0.25 inches beyond the periphery of the frame. The thickness of the ePTFE may be between about 0.001 inches to about 0.25 inches and preferably in the range of about 0.005 inches to about 0.025 inches. The IND of each encapsulating material may be in the range of about $5\mu$ to about $200\mu$ with the higher value being more suited to encouraging tissue ingrowth but exhibiting less strength. The IND of each encapsulating material may be different to effect different mechanical properties on either side of the device, mechanical bonding, and fixation. The ePTFE material should preferably be of an unprocessed extrudate variety that has not been subjected to further surface treatments such as sintering and exhibits uniform physical and chemical properties throughout.

Besides exhibiting superior elasticity, strength, and biocompatibility, the material chosen for the barrier frame 53 will preferably be able to withstand the temperatures and exposure times required to monolithically encapsultate it in the encapsulating material 51. In this preferred embodiment, a nickel titanium alloy is chosen.

Figure 7:
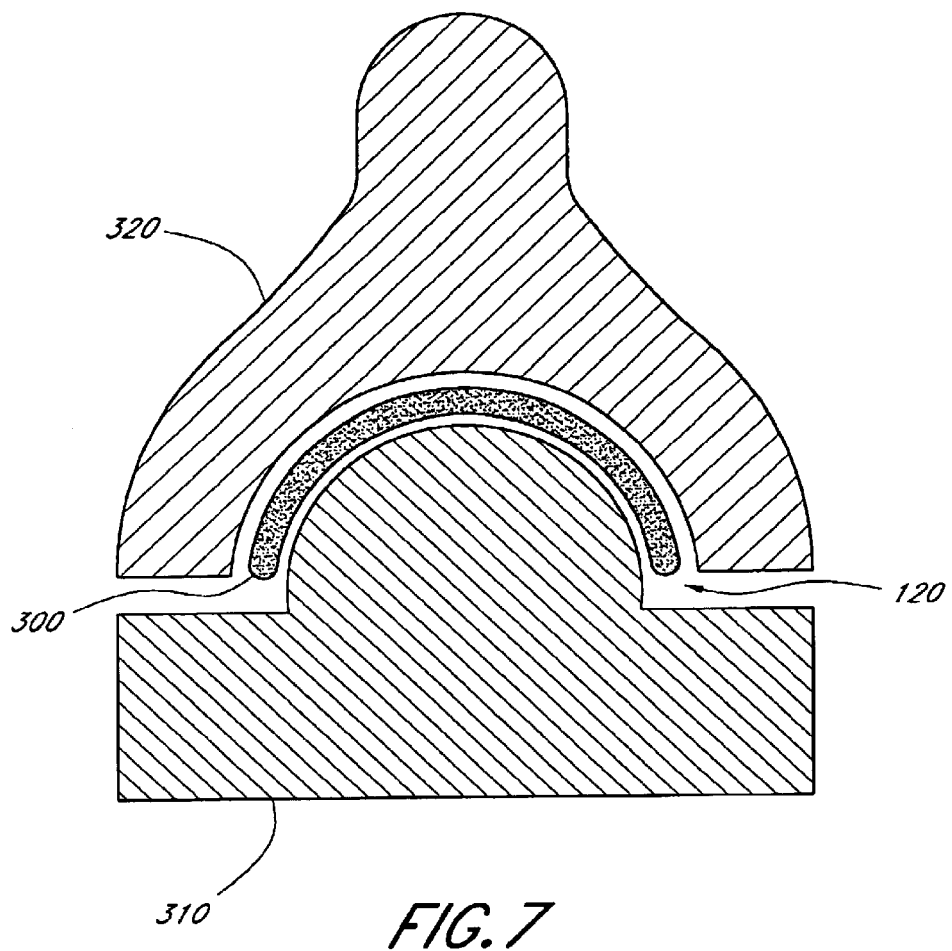
FIG. 7 shows a cross sectional view of the mandrel, the sandwich-like arrangement of a first encapsulating membrane, the barrier frame, and a second encapsulating membrane, and a mandrel cover. The arrangement depicted can also be formed by a frame disposed within a tubular encapsulating membrane.

FIG. 7 shows a method of encapsulating the frame 53 within the encapsulating material 51. The encapsulating material 51 can be further comprised of either 2 sheets, i.e. a first encapsulating material 54 and a second encapsulating material 55, formed as a tube, or as a larger sheet capable of folding over the frame 53. Referring back to the FIG. 7, a sandwich-like arrangement 300 of the barrier frame 53 disposed between a first 54 and second encapsulating material 55, is placed on the hemi circular or curved face of a mandrel 310. A cover 320 is placed on top of the sandwich-like arrangement 300 and force is applied sufficient to cause the edges of the encapsulating material 51 to contact each other. The contact may be continuous around the periphery of the barrier frame 53 and may even form contacts through the holes in the complex geometry of the barrier frame 53. Also, the surface of the mandrel face 310 or cover 320 may contain recesses which serve to not provide pressure or force at locations where bonding is not desired to further permit the barrier frame 53 to move within encapsulating first and second encapsulating material 51. In order to create bonds at the contact points, the arrangement 300, mandrel 310, and cover 320 are heated to a temperature around the crystalline melting point of ePTFE, 327° Celsius. Also, it may be preferable to utilize a range of temperatures from 325 to 375° Celsius to control the rate of bonding. Also, the barrier can be preheated by subjecting it to 300° Celsius for around one minute to decrease the time that the arrangement 300, mandrel 310, and cover 320 must be heated. The exact time required for the desired bonding is quite variable and dependant on several factors including the mass and consistency of the mandrel and geometry of the barrier frame 53. Accordingly, one of ordinary skill could easily determine the proper time for a particular set-up taking care not overheat the ePTFE and cause it to degrade or adversely affect the heat treatment of the frame 53.

This method can alternatively be practiced using a tube or folded sheet of ePTFE so that fewer edges need form a bond to effectively encapsulate the frame 53. Using a folded sheet encapsulating material 51 can also be used to create a partially covered frame 53. Alternatively, using a tube is particularly advantageous in forming the arrangement 300 since the step of applying the second encapsulating material 55 is not necessary. The frame 53 is simply inserted in the hollow encapsulating material 51 and then heated in the covered mandrel.

Another method of making the device 120 comprises the adhesion of the first encapsulating material 54 to the second encapsulating material 55 using aqueous PTFE. Here a sandwich of first encapsulating material/aqueous PTFE/barrier frame/aqueous PTFE/second encapsulating material is made and then heated to the melting point of the aqueous PTFE, around 325°, which is less than the sintering temperature of the encapsulating material. In this way, the water and wetting agents are burned off and the PTFE particles melt and mechanically bond to the surfaces of the first and second encapsulating material 51.

Aqueous PTFE or other adhesion material may be used to encapsulate the frame 53 within a tube, folded single sheet, or between two sheets of the encapsulating material 51. Also, selected portions of the encapsulating material 51 can be coated with the adhesion material depending on the degree and location of the bonding one desires. For example, a single sheet encapsulating material 51 on a either side of the frame 53 may be attached with the aqueous PTFE by depositing it along either or both sides of the frame 53 allowing it to contact the encapsulating material through and around the frame 53 and heating it until mechanical bonds form. Other adhesion material may also be used to bond, either chemically or mechanically, the encapsulating material 51 to itself or the frame 53. Examples of adhesion material include, but are not limited to, common medical adhesives like cyanoacrylate, light curing adhesives, urethane, epoxy, and silicone. Further examples include polyamides, polyimides, silicones, polyurethane, natural rubber, latex and other fluoropolymers such PFAs and FEPs.

Heat shrinking PTFE wrap or tubing around the barrier frame 53 is yet another way to provide a biocompatible and resilient encapsulation. PTFE begins to shrink around 340° Celsius and completes its recovery during the cooling cycle. In one method, the barrier frame 53 can be preheated to around 340° Celsius and a slightly larger tube may be placed over it whereupon the tube shrinks in place upon contact and when cooled provides a smooth coverage leaving only two small uncovered spots at the tails of the barrier 53. These uncovered spots do not affect the devices ability to retain intervertebral disc material, pressure, or height. Using the methods described above, these ends may also be sutured or welded. Alternatively, an assembly of the barrier frame 53 placed within a slightly larger tube may be positioned on a mandrel 310 with a hemi circular face and covered with a mandrel cover 320 and then heated to around 340° Celsius until the PTFE shrink fits around barrier frame 53.

As disclosed above, partial encapsulation or covering of the frame 53 may be accomplished with these methods. For example, an encapsulating material 51 comprised of ePTFE disposed around the fingers 162 and face of the device 120 but leaving the center of the frame 53 exposed may be advantageous for delivery and placement of the device. By leaving a portion of the frame 53 uncovered, a solid contact point is provided that can be used to couple the device 120 to a delivery instrument. Alternatively, the encapsulating material 51 can be designed to have a channel within itself or covering a channel in the frame 53 that accepts a guide or probe from the delivery instrument.

An alternative method is comprised of applying an extremely thin, highly expanded PTFE film around the frame 53. By wrapping the film transversely around the long axis of the frame radial strength can be added to the underlying longitudinal strength of the PTFE tube. The radially wrapped tube can then be placed on the mandrel face 310 and compressed and heated to 350–390° Celsius in conjunction with the mandrel cover. The heating process will allow the film to shrink and bond to the underlying PTFE substrate and encapsulating the frame 53. The additional film will provide radial strength and minimize any potential for protrusion of the frame through the PTFE. In addition, while the film wrapping is being performed a template can be placed on the convex side of the PTFE tube. Over-wrapping of this tube will allow for creation of a pocket on the convex side of the frame 53. This pocket in conjunction with the windows left in the tube covering would allow for attachment of a delivery instrument to the convex side of the frame. An important manufacturing consideration of this application method is the need for such high temperatures for sufficient bonding of the PTFE film and its deleterious effects on the underlying metallic substrate. Using an FEP/PTFE laminated film with corresponding lower bonding temperatures of 300–320° Celsius can reduce this effect.

Subsequent to the application of pressure to the first encapsulating material and/or semicircular frame and/or second encapsulating material assembly and sintering the same to mechanically bond the ePTFE, the mandrel cover is removed and the device is removed from the mandrel. In this state the device is now ready for implantation into an intervertebral disc. In use, the encapsulated barrier is folded or crimped via stress-induced martinsite or heat induced martinsite into a delivery cannula so that it may be inserted through a naturally occurring or minimally invasive iatrogenic hole. The unique structure and composition of the device allows it to endure a ninety-degree bend and be delivered parallel to the anular lamellae and in front of the anular defect.

While references are made to a semi-circular frame and matching mandrels, alternative cross sectional shapes of the frame of the present invention may be employed to achieve various stiffness or pressure response characteristics of the overall device. As an example, compound curves may be desirable to create multiple convexities and concavities in the frame. Alternatively, a single concavity with varying radii of curvature may be employed rather than the single radius of a semi-circle. Appropriately shaped mandrels may be used with any of these shapes to achieve the encapsulation methods described above.

Accordingly, utilizing the methods described herein will provide a biocompatible and durable implant. In a preferred embodiment, the implant is folded or crimped into a delivery cannula so that it may be inserted through a naturally occurring or minimally invasive iatrogenic hole. Among other features, the unique structure and composition of the device allows it to endure a ninety-degree bend and to be delivered parallel to the anular lamellae and in front of the anular defect.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of making an intervertebral prosthesis comprising the steps of:
placing a first biocompatible encapsulating material over a heatable mold with a curved face, said first biocompatible encapsulating material sized to extend from about 0.1 mm to about 0.5 mm beyond the edges of a barrier frame;
placing the barrier frame on the first encapsulating material, said barrier frame dimensioned to span beyond the distance defined by the maximum distance between an inferior and superior endplate of a normal intervertebral disc and to extend circumferentially along the lateral and posterior surfaces of an anulus, wherein at least a portion of said barrier has a curvilinear cross-section and is comprised of nickel titanium alloy;
placing a second encapsulating material on top of the barrier frame, said second biocompatible encapsulating material designed to extend from about 0.1 mm to about 5 mm beyond the edges of the barrier frame;
placing a mold cover with a concave interior corresponding to face of the mold on top of the second encapsulating material and applying force such that the edges of the first and second encapsulating material form one or more contact points with each other around the barrier frame; and
heating the base and the cover and the frame sandwiched between the first and the second encapsulating material until the first and second encapsulating material bond to each other at said one or more contact points.

2. The method of claim 1, wherein said placing a first biocompatible encapsulating material over a heatable mold with a curved face comprises placing a first biocompatible encapsulating material over a heatable mold with a curved face having a first axis and a second axis which are perpendicular to one another.

3. The method of claim 2, wherein said first axis is a longitudinal axis having a first radius of curvature and said second axis is a transverse axis having a second radius of curvature.

4. The method of claim 3, wherein said first radius of curvature has a range of about 0.2 cm to about 2.5 cm and said second radius of curvature has a range of about 3.0 cm to about 5.0 cm.

5. The method of claim 1, wherein said curvilinear cross-section is a semi-circular cross-section.

6. The method of claim 1, wherein said first biocompatible encapsulating material comprises ePTFE.

7. The method of claim 1, wherein said first biocompatible encapsulating material comprises a biological material selected from the group consisting of one or more of the following: keratin, collagen, bio-engineered anulus fibrosus, and protein polymers.

8. The method of claim 1, wherein said first biocompatible encapsulating material comprises a synthetic material selected from the group consisting of one or more of the following: polyamides, polyimides, silicones, polyurethane, natural rubber, latex, perfluoroalkoxy and fluorinated ethylene-propylene.

9. The method of claim 1, wherein said first biocompatible encapsulating material is constructed of the same material as said second biocompatible encapsulating material.

* * * * *